US006915240B2

(12) United States Patent
Rabinowitz et al.

(10) Patent No.: US 6,915,240 B2
(45) Date of Patent: Jul. 5, 2005

(54) SYSTEM AND METHOD OF DATA REDUCTION FOR IMPROVED EXPONENTIAL DECAY MEASUREMENTS

(75) Inventors: Paul Rabinowitz, Bridgewater, NJ (US); Kevin Lehmann, Lawrenceville, NJ (US)

(73) Assignee: Princeton University, Princeton, NJ (US)

( * ) Notice: Subject to any disclaimer, the term of this patent is extended or adjusted under 35 U.S.C. 154(b) by 156 days.

(21) Appl. No.: 09/998,518

(22) Filed: Nov. 29, 2001

(65) Prior Publication Data

US 2003/0101026 A1 May 29, 2003

(51) Int. Cl.[7] ............................................. G06F 15/00
(52) U.S. Cl. ..................................... 702/189; 250/343
(58) Field of Search ........................ 702/66, 70, 74–76, 702/111, 189–191, 193–195, 197; 356/437–440, 432; 250/343

(56) References Cited

U.S. PATENT DOCUMENTS

| | | | | |
|---|---|---|---|---|
| 4,745,279 | A | * 5/1988 | Karkar et al. | 250/343 |
| 5,291,426 | A | * 3/1994 | Collins et al. | 702/195 |
| 5,528,040 | A | * 6/1996 | Lehmann | 250/343 |
| 5,920,641 | A | * 7/1999 | Ueberreiter et al. | 382/125 |
| 5,973,782 | A | * 10/1999 | Bomse | 356/451 |
| 6,135,952 | A | * 10/2000 | Coetzee | 600/336 |
| 6,233,052 | B1 | * 5/2001 | Zare et al. | 356/437 |
| 6,532,071 | B2 | * 3/2003 | Zare et al. | 356/437 |

OTHER PUBLICATIONS

Yan et al., "Trace gas detection with CW cavity ring–down laser absorption spectroscopy", Sep. 2000, Advanced Semiconductor Manufacturing Conference and Workshop, 2000 IEEE/SEMI, pp. 203–206.*
Dudek et al., "Using CW–CRDS for trace gas detection", Jul. 2000, Electronic–Enhanced Optics, Optical Sensing in Semiconductor Manufacturing, Electro–Optics in Space, Broadband Optical Networks, 2000. Digest of the LEOS Summer, pp. 9–10.*
Daponte et al., "Detection of echoes using time–frequency analysis techniques", Feb. 1996, Instrumentation and Measurement, IEEE Transactions on, vol.: 45 Issue: 1, pp. 30–40.*
Himel et al., "An adaptive noise cancelling system used for beam control at the Stanford Linear Accelerator Center", May 1993, Real–Time Applications, 1993., Proceedings of the IEEE Workshop on, pp. 212–215.*
William H. Press, et al., "Numerical Recipes," , pp. 521–528, Cambridge University Press, 1986, New York, NY.
Philip R. Bevington and D. Keith Robinson, "Data Reduction and Error Analysis For The Physical Sciences," pp. 134–140, Second Edition, McGraw–Hill, Inc. New York, NY.
Roger D. Van Zee, et al., "Pulsed single–mode cavity ring–down spectroscopy," Applied Optics, 38 (18), 3951–3960 (1999).

* cited by examiner

*Primary Examiner*—Marc S. Hoff
*Assistant Examiner*—Mary Catherine Baran
(74) *Attorney, Agent, or Firm*—Goodwin Procter LLP

(57) ABSTRACT

A novel system and method for data reduction for improved exponential decay rate measurement in the present of excess low frequency noise. The system and method fit the tail of a record to a straight line wherein the straight line is extrapolated to the entire record and then subtracted from the initial data points before a logarithmic transformation is taken.

13 Claims, 13 Drawing Sheets

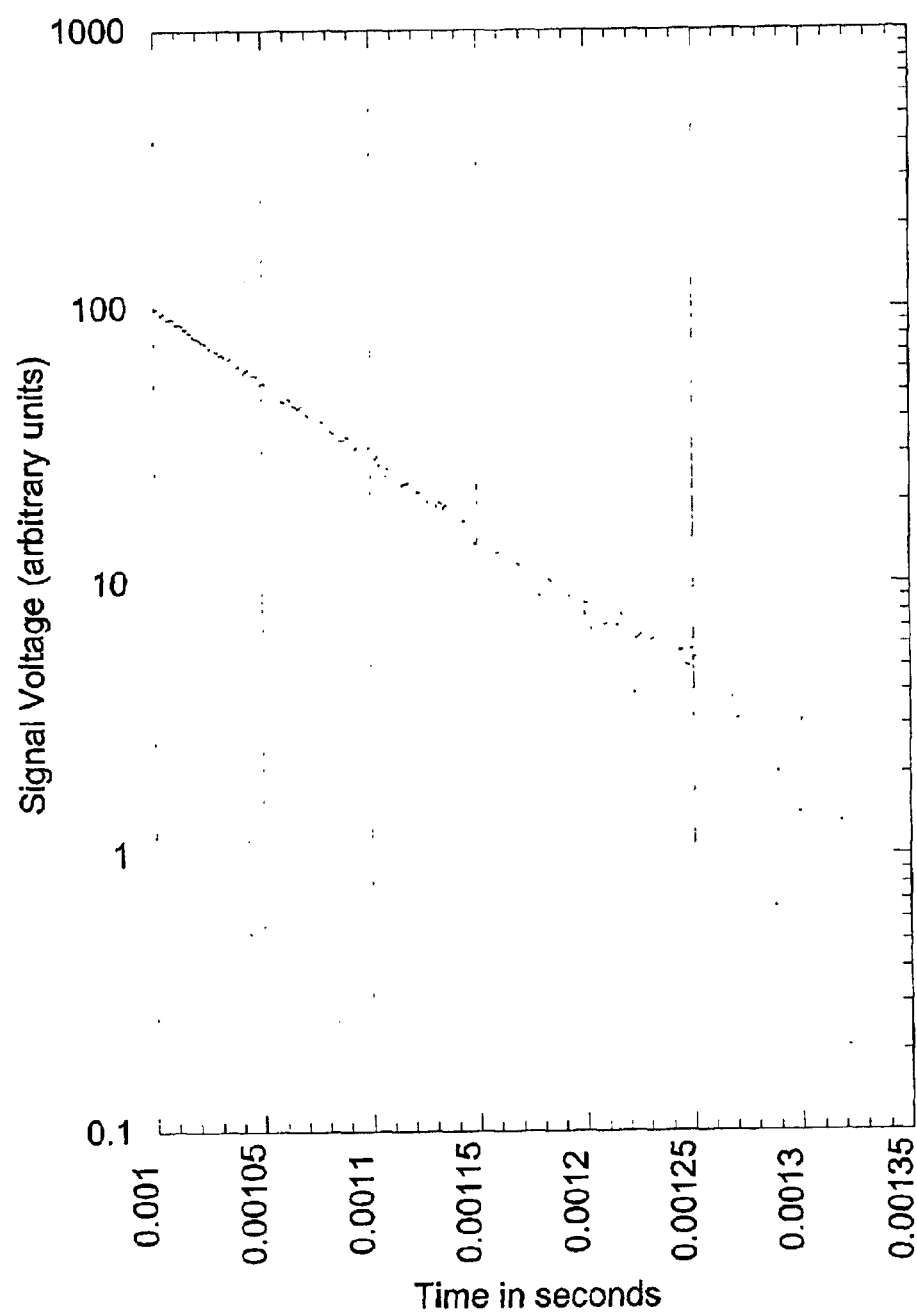

US 6,915,240 B2

SYSTEM AND METHOD OF DATA REDUCTION FOR IMPROVED EXPONENTIAL DECAY MEASUREMENTS

RELATED APPLICATIONS

This application incorporates by reference U.S. Pat. No. 5,528,040 to Lehmann in its entirety to the extent it is not inconsistent with the application presented herein.

FIELD OF THE INVENTION

The present invention is directed toward a data processing system and method where a signal is contaminated by noise of a frequency much less than those that dominate the expected signal itself. More specifically, the present invention is directed toward a system and method for optimized data processing in ring-down spectroscopy.

BACKGROUND OF THE INVENTION

Ring-down spectroscopy determines the concentration of an absorbing species within an optical resonator by the measurement of a single parameter, the exponential decay rate of radiation in that resonator. Invariably, regardless of the experimental details of the particular scheme that is used, the measurement consists of detecting the radiation as it decays with an optical square law detector, amplifying the detected signal, and then processing the resulting record to determine the decay rate.

Because of the presence of fundamental broadband (white) noise in measurements, whether dominantly from the detector, the amplifier or the light itself, fluctuation and error occur in the measurement and the decay rate must be determined by one of a number of possible statistical regression (curve fitting) techniques. Often, a single measurement is insufficient for the desired precision so instead the measurement is repeated many times to produce an ensemble of records from which a more precise averaged value of the desired parameter can be obtained, provided there is no drift in the measured quantity. In the averaging process the improvement in precision is proportional to the square root of the number of records. In a practical instrument, the speed of measurement is important and the processing that achieves the desired precision with the fewest records (i.e. the shortest time) represents the preferred process.

For instruments operating in various real-world industrial environments there may often be sources of noise beyond those noted. For example, the ubiquitous sixty-Hertz line frequency from transformers, imbalanced grounds, and close proximity heavy duty machinery, can be picked-up and produce noise spectral density well in excess of the level of fundamental white noise. Careful design of the electronics package has been shown to reduce, but rarely eliminate, the effects of external noise sources. Numerical simulations have established that sixty-Hertz noise signals with a root mean square ("RMS") amplitude comparable to that of the broadband noise, but unsynchronized with respect to the initiation of the ring-down signal, can more than quintuple the uncertainty in the measurement, resulting in a nearly twenty-five fold increase in the number of records needed to achieve the desired precision.

Therefore, it is an object of the present invention to provide a system and method that greatly reduce the effect of such noise, reducing the effect for the case sited to a mere one and a half fold increase in the number of records needed to achieve the desired precision.

Additionally, it is another object of the present invention to achieve a significant improvement in the precision of filtering any excess noise components that have a period that is greater than four times the length of a record.

SUMMARY OF THE INVENTION

The present invention overcomes the limitations of the above prior art techniques for measuring exponential decays in the presence of excess low frequency noise.

The present invention is an efficient addition to existing systems and methods for data processing of ring-down signals that correct for errors introduced by low frequency noise that may be present, e.g., due to line frequency pick-up.

In the present invention, the required length of a record is determined by a number of factors, including the empty resonator decay time and the ratio of the signal amplitude to the RMS noise background. Typically a record length is several times longer than the time for the exponential signal to decay to within the RMS level of the background white noise.

The best fit parameters of a function that is nonlinear cannot be directly calculated in general, forcing the use of iteration techniques, that require initial guesses for the parameters, that can consume large amounts of computer time, and ultimately can fail to find a result. Such a limitation of the prior art is described in "Numerical Recipes," William H. Press at al., page 521, Cambridge University Press, 1986, New York, N.Y. Fortunately, in the case of an exponential decay to a known background level, it is possible to transform the function by a logarithmic transformation into a linear one that easily can be fit. This tecimique is described in "Data Reduction and Error Analysis For The Physical Sciences," Philip R. Bevington and D. Keith Robinson, page 134, Second Edition, McGraw-Hill, Inc. New York, N.Y. This method can be applied to the digitized data after the subtraction of any DC level that is present from the electronic processing. That level may be obtained at the beginning of the measurement process by taking a measurement with no ring-down signal or preferably on each record to eliminate possible drift by measuring the DC offset far into the exponential decay where the signal has fallen significantly below the background noise amplitude. The variance in that level is used as an estimate for the variance of the data points and in the subsequent weighting of the linearized fit, as shown in "Pulsed, single-mode cavity ring-down spectroscopy," Roger D. van Zee et al., Applied Optics, 38, 3951(1999).

Once the data has been conditioned by removal of the DC level, an additional conditioning is necessary before the logarithmic transformation can be made. Data points that are of zero value or negative have no real logarithm and are thus removed. These data points first appear once the exponential decaying signal is comparable with the noise and define the data cutoff point for fitting. In addition, a few of the initial data points are also removed because of transients in the radiation switching. The estimates for the parameters are then obtained from the weighted linear least squares fit to the logarithm of the conditioned data. Here, where $y = A \exp\{-rt\}$, the amplitude, A, and the decay rate, r, are the parameters. The variables are y, the voltage above background, and t, the time after initiation of the ring-down.

When only white noise is present, the resulting estimates for the parameters and their variances follow the theoretical statistical predictions. However when a relatively low level of excess noise is present at low frequencies, there is a significant increase in the variance of the parameters. Further, the standard statistical prediction for the uncertainty of the fitted decay rate substantially underestimates the true uncertainty, as found, for example, by looking at the variance of the decay rates extracted from an ensemble of identical (except for noise) decay events.

In general, one possibility to compensate for excess 60 Hz noise alone is to include in the fitting routine an additional sinusoidal function that is a linear composite of a sine and a cosine function. Unfortunately, this addition to the overall equations would make them fully nonlinear and thus drastically increase the computational resources required to obtain the desired solution.

An efficient simple solution of the present invention is available by recognizing that the effect of a low frequency sinusoidal signal to the first order is to produce an overall slope to the record. The present invention fits the tail of the record to a straight line. The line is extrapolated to the entire record and then subtracted from the initial data points before the logarithmic transformation is performed. As long as the record is smaller than a quarter period of the sinusoid, a significant improvement is obtained. This makes the system and method more robust since it will correct for low frequency noise regardless of the exact frequency of that noise, or even if it is made up of several frequency components, provided the period of the highest frequency is greater than four times the record length.

BRIEF DESCRIPTION OF THE DRAWINGS

Exemplary embodiments of the invention are described below with reference to the following accompanying drawings.

FIG. 13 is a graph on a logarithmic scale of the data in FIG. 12.

DETAILED DESCRIPTION OF THE PRESENT INVENTION

Figure 1:
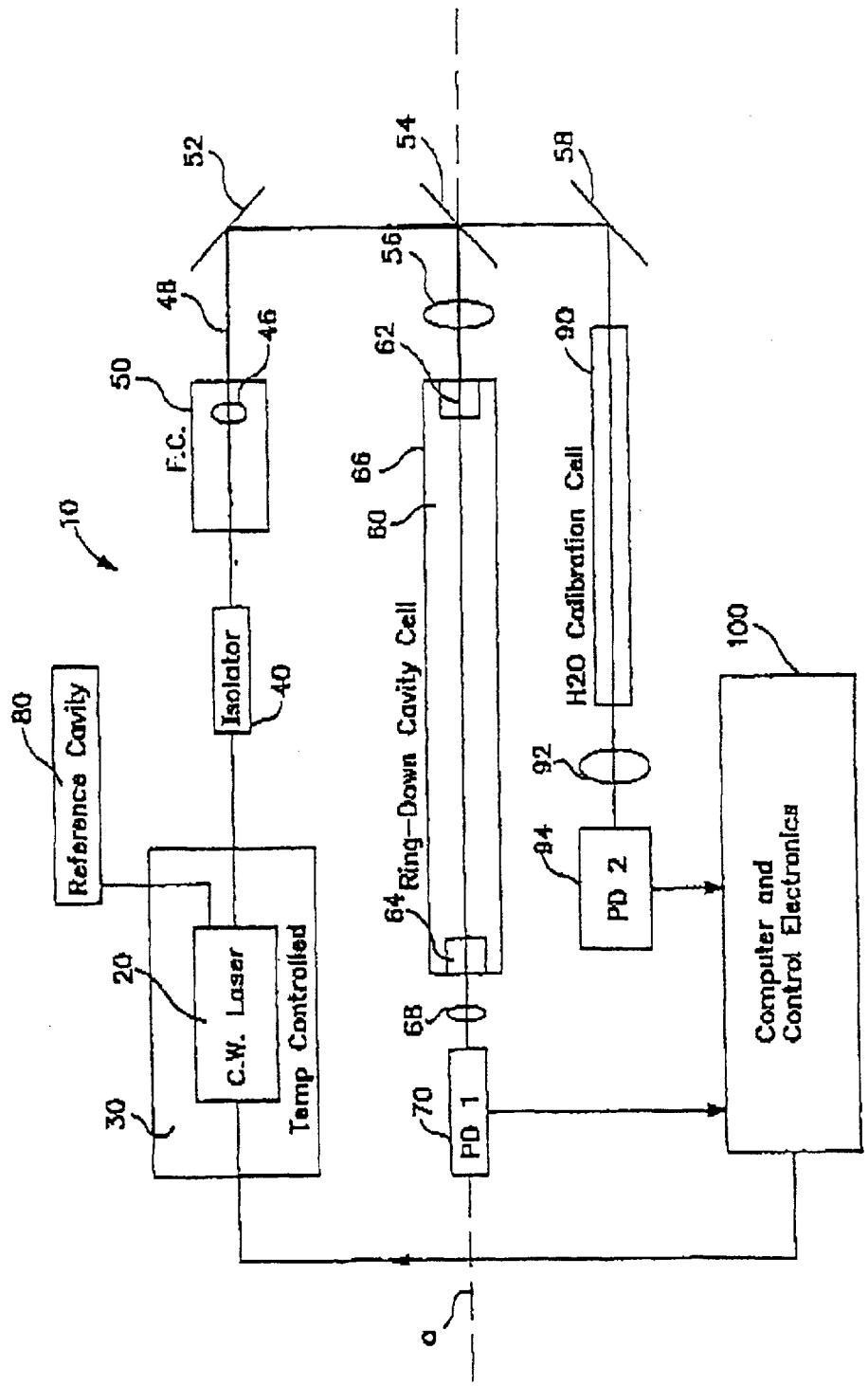
FIG. 1 is a schematic diagram of a sample apparatus suitable for implementing the methodologies and systems of the present invention.

The present system and method has been tested with experimental data and with data generated from a computer model. In each case, a significant improvement was measured; with the computer model the improvement was quantified.

Appendix A is provided as the source code used in generating the computer data. A model of a ring-down signal with noise is created to mimic experimental data obtained from a photodector and preamplifier applied to an analog to digital converter. It is then fit with the new and improved algorithm that subtracts a line that is fit to the background before applying the standard algorithm and compares that fit with one that simply uses a constant for baseline subtraction.

For the computer program, exponential decays of tau=80 microseconds were used. A peak signal was chosen. Uncorrelated Gaussian noise was added. And a dc offset and sixty Hz noise were added. As in real experiments the data is sampled every microsecond.

The following section illustrates results from the source code written for the algorithm of the present invention. This source code, given in Appendix A, is written in the Fortran 77 Programming Language. The specific type of high level language used to implement the algorithm is not particularly relevant to the present invention, since it will be apparent that almost any type of high level language such as Microsoft's VISUAL BASIC™, VISUAL C or C++ could be used instead. The following brief example of the application of the algorithm to synthetically generated data demonstrates the improvement in the decay time variance with the present invention.

Tests were conducted using the system and method of the present invention. The test results were computed using 500 independent ring-downs with the RMS of the 60 Hz equal to the RMS of the Gaussian white noise. These results are provided as Appendix B. As indicated on the bottom of the table in Appendix B, the squared ratio of the ensemble sigma tau is 19.77. That ratio shows that to achieve a given precision in tau, in the prior art, one needs 19.77 times as much averaging using the standard algorithm compared with the new system and method of the present invention. The run of 500 independent ring-downs was repeated ten (10) times to develop a statistic on the improvement for this set of parameters and the result was that the average improvement of the ensemble sigma tau was by a factor of 18.98 with a standard deviation of 1.42. As expected, if the 60 Hz noise signal gets smaller, the improvement also gets smaller. However, the significance of the result is that the time taken to make a measurement of a given precision is reduced by that ratio. To be most effective, the low frequency noise that the algorithm corrects for should be less than or equal to 0.42/Tr, where Tr is the length of the record in seconds.

Chosen values for the sample are as follows: amp=800.00; 60 Hz-RMS=3.50 offset=10.00; tau=80.00; and gauss RMS=3.5. These values were typical of those measured in the laboratory, where the amplitudes and voltage levels are measured in millivolts, and time in microseconds.

The output of the source code produces the table in Appendix B. The resulting values follow: average tau=80.13, sigma tau=0.8777, average reduced $(chi)^2$=1.099, average amp=799.27, sigma amp=1.0028, and the squared ratio of sigma tau from the traditional and new algorithm=19.78.

An example of a cavity ring-down spectroscopy (CRDS) system is shown in FIG. 1, as taught in U.S. Pat. No. 5,528,040 by Lehmann, to provide a better understanding of the present invention. The apparatus of FIG. 1 can be used in conjunction with the present invention, although other variations of the system depicted are contemplated. For example, the algorithm can be applied to pulsed laser ring-down systems, as well. The system described is provided only as an example and not as a limitation with respect to the ring-down system contemplated by the present invention.

Turning to FIG. 1, an example of a prior art cavity ring-down spectroscopy (CRDS) system is shown. Light is generated from a narrow band, tunable, continuous wave diode laser 20. Single mode diode lasers are well known in the art and are produced and commercialized for use in instruments such as described herein. The laser 20 can be a single mode, continuous wave diode laser tunable in a particular wavelength region.

Laser 20 may alternately be one of a number of different types of lasers such as a distributed feedback (DFB) laser, an "external cavity" diode laser or an optical fiber laser. Laser 20 can be temperature tuned by a temperature controller 30.

An isolator 40 is positioned in front of and in line with the radiation emitted from laser 20. Isolator 40 provides a one-way transmission path, allowing radiation to travel away from laser 20 but preventing radiation from traveling in the opposite direction. Thus, isolator 40 protects laser 20 from back reflections or optical feedback, which tend to increase laser noise.

The light emitted from laser 20 must be coupled as efficiently as possible into the optical fiber 48. A single mode fiber coupler ("F.C.") 50 is provided for that purpose. Fiber coupler 50 is positioned in front of and in line with isolator 40. Fiber coupler 50 receives and holds optical fiber 48 and directs the radiation emitted from laser 20 toward and through a first lens 46. First lens 46 collects and focuses the radiation. Because the beam pattern emitted by laser 20 does not perfectly match the pattern of light propagating in optical fiber 48, there is an inevitable mismatch loss. Fiber coupler 50 reduces this loss to about 3 db.

The laser radiation is approximately mode-matched into a ring-down cavity ("RDC") cell 60. A reflective mirror 52 directs the radiation toward a beam splitter 54. Beam splitter 54 directs at least 50%, and typically about 90%, of the radiation through a second lens 56. Second lens 56 collects and focuses the radiation into cell 60. The remaining radiation, typically 10%, passes through beam splitter 54 and is directed by a reflective mirror 58 into a water calibration cell 90—also referred to as a wavelength select meter.

Calibration cell 90 is used to tune laser 20. The radiation, which is transmitted through calibration cell 90 is directed toward and through a fourth lens 92. Fourth lens 92 is aligned between calibration cell 90 and a second photodetector 94 (PD 2). Photodetector 94 provides input to computer and control electronics 100.

Cell 60 is made from two, highly reflective mirrors 62, 64, with radii of curvature of about 1 meter and separated by a distance, d, of about 1 meter. This distance was chosen based upon stock available mirrors; shorter cells could easily be built for a field-deployable system with only a modest decrease in sensitivity.

The length of cell 60, L, is a compromise between opposing requirements. Because RDC decay time is dominated by mirror losses and transmissivity, the cavity length should be maximized. On the other hand, the maximum length is determined by space considerations and by the requirement that the cavity be stable with respect to beam size. According to the theory of stable resonators, in the case of two mirrors with the same radius of curvature, r, the transverse modes of the resonator have a finite size if the cavity length is less than 2r (their size diverges for this value).

Mirrors 62, 64 constitute the input and output windows of cell 60. The sample gas under study flows through a narrow tube 66 (1 cm$^2$ cross section) that is coaxial with the optical axis, a, of cell 60. Mirrors 62, 64 are placed on adjustable flanges or mounts (not shown) that are sealed with vacuum tight bellows (also not shown) to allow adjustment of the optical alignment of cell 60.

Mirrors 62, 64 have a high-reflectivity dielectric coating and are oriented with the coating facing inside the cavity formed by cell 60. A small fraction of laser light enters cell 60 through front mirror 62 and "rings" back and forth inside the cavity of cell 60. The mechanical alignment of the mirrors is most forgiving when the RDC is close to confocal (L=r) and becomes extremely critical when either the concentric (L=2r) or planar (L is much less than r) limits are approached.

Light transmitted through rear mirror 64 (the reflector) of cell 60 is directed toward and through a third lens 68 and, in turn, imaged onto a first photodetector 70 (PD 1). Photodetectors 70, 94 may be thermoelectrically cooled.

Figure 2:
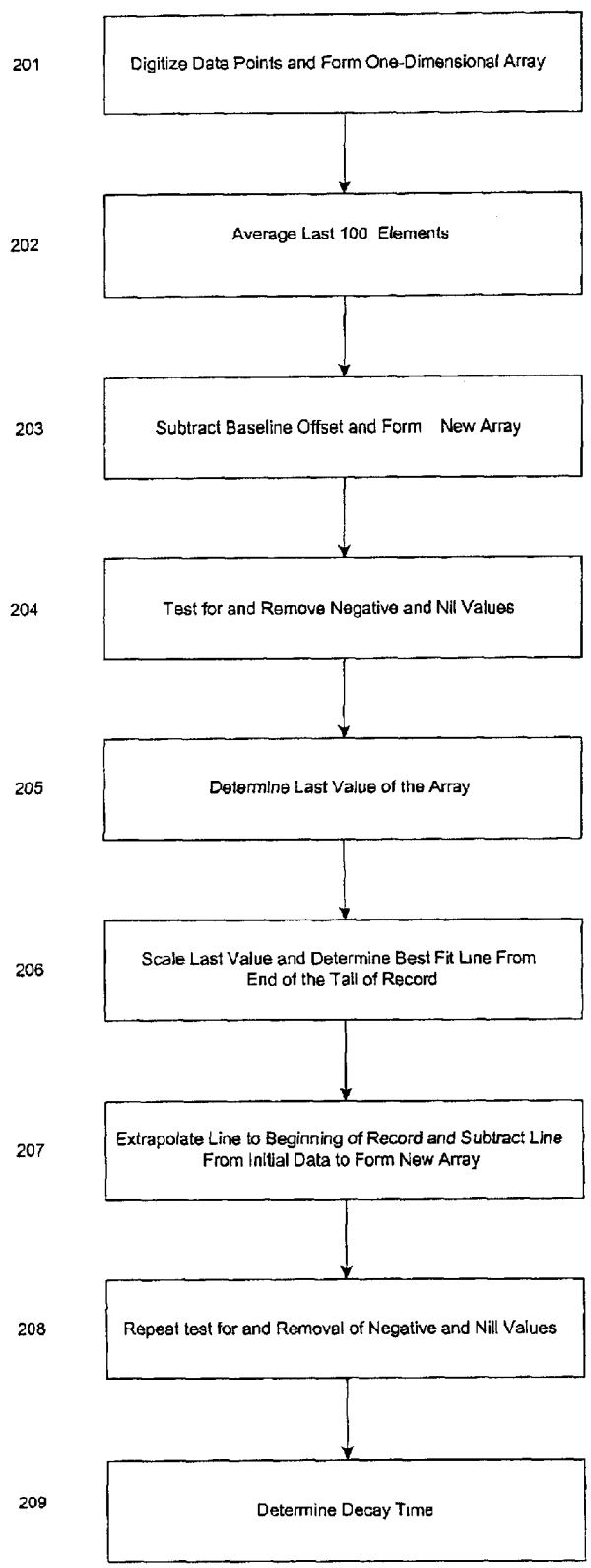
FIG. 2 is a flow diagram illustrating certain methodical aspects of the present invention.

As shown in FIG. 2, an exemplary embodiment of the present invention can be outlined as follows: 201: Ring-down data are digitized by an A-D converter and read into a computer as a one-dimensional array. 202: The last hundred elements or so are averaged to obtain a DC offset and an estimate of the RMS noise. 203: The baseline offset is subtracted from the initial data to form a new array. 204: Starting at the first elements of the new array the data is tested for a zero value or a sign change. 205: The last point before such a change is the maximum array element that can be used in the logarithmic transformation. 206: The maximum array element number is scaled by a factor greater than unity, and array elements greater than this value are fit to a straight line and a new estimate of the RMS noise determined. 207: The line is extrapolated to the beginning of the record and subtracted from the initial data to produce a new array. 208: Once again the array is examined for a sign change to obtain the maximum abscissa for the logarithmic transformation. 209: After removal of the initial few points in the switching transient, a weighted least squares fit of the logarithmic transformed data to a straight line determines the decay time and the amplitude of the ring-down signal and provides estimates of the precision.

Steps 206–208 provide the improved performance in the presence of low frequency noise as taught by the present invention.

As an example of the present invention, a model of a ring-down signal with noise is created to mimic experimental data obtained from a photodetector and preamplifier applied to an A to D converter. It is then fit with the novel algorithm of the present invention that subtracts a line that is fit to the background before applying the standard algorithm and compares that fit with one that simply uses a constant for baseline subtraction as taught in the prior art. Exponential decays of tau=80 microseconds are used, a peak signal is chosen, Gaussian noise is added, a dc offset is added and then sixty Hz noise is added. The data is sampled every microsecond. Lastly with this data, one iteration of the prior art fit is used and the present invention is used and then the results are compared.

To produce the model data, first, an arbitrary integer is selected for the pseudo random number generator seed. Next, values for the Gaussian white noise in millivolts, the signal amplitude, the 60-Hertz RMS level, and the DC offset voltage are provided along with the decay time (tau). In one embodiment the inverse of the decay rate, a decay time of 80 microseconds is used. The 60-Hertz RMS level must also be converted to amplitude from an RMS value.

Next the records are fit to the exponential, first using a weighted log transformation. To do this, the average value for the last 100 points or so of each decay is determined to establish a baseline. For these points, the signal has fallen off many orders of magnitude below the noise. Once the baseline is established, it is subtracted from the data and sigma is determined from those last 100 or so points, where sigma is calculated from the baseline fluctuation. The first non-positive array element is identified to determine the range of data that can be transformed logarithmically and to first order the time for the exponential decay to reach the noise level.

Now, data for determining the line that is to be subtracted from the initial ring-down data is selected from those data points beginning at twice the time that the exponential decays to the noise level and continuing to the end of the record. This data begins at an array number designates as ($i_0$). In a preferred embodiment, no less than 200 points should be used for the fit, which may reduce the factor of two in time by which the data is selected. At this point, the ring-down signal is as far below the noise as it was above the noise initially. This data is fit to a straight line, which is then subtracted from the initial data rather than just a constant as is taught in the prior art. The mathematical formula for a straight line is y=(m)x+b, where y is the ordinate and x the abscissa, and the parameters m and b are the slope and intercept respectively. In the present case, the ordinate is the array of points, s(i), and the abscissa the array number, (i), beginning at the value ($i_0$) and continuing to the end of the record.

Once the line is determined, it is subtracted from the initial data. This includes finding the new maximum value of i (determined by the first non positive point) the running variable of the digitized record. Next, the logarithm of the reduced data is found up to the maximum value of i. This transformed data is used to calculate the slope and intercept of the line with a weighted average of the points, as described by Bevington. In addition, the reduced average chi$^2$ and sigma tau are calculated. Lastly, the decay rate is to be converted to decay time or tau.

At this point, new data to produce a new ring-down curve for an ensemble is provided using the same procedure as before with of course new and independent values for the noise. Appendix B displays sequentially the calculated results for each element of the ensemble of ring-downs; the time constant, tau; the amplitude, amp; the number of points used in the fit, num points; the standard deviation of the noise, sigma; the reduced chisq; the standard deviation of the time constant, sigma tau; and the standard deviation of the amplitude, sigma amp.

Once these values are all determined, this process can be repeated using a constant baseline for subtraction instead of the method of the present invention which establishes a line to fit for baseline subtraction.

Given the parameters for the dc offset, decay time, signal amplitude, 60-hz amplitude, RMS random Gaussian noise, and pseudo random number seed, an array, s(i), that represents the ring-down voltage is returned. As can be seen in the results of Appendix B, comparing the results with the weighted best fit line values for baseline subtraction to the values generated using a constant baseline subtraction to determine decay rates, the present invention provides a marked improvement over the prior art.

FIGS. 3–12 depict a ring-down data signal sequence data model. For each figure the y-axis of the depicted data models represents signal voltage in arbitrary units and the x-axis represents time in units of seconds.

Figure 3:
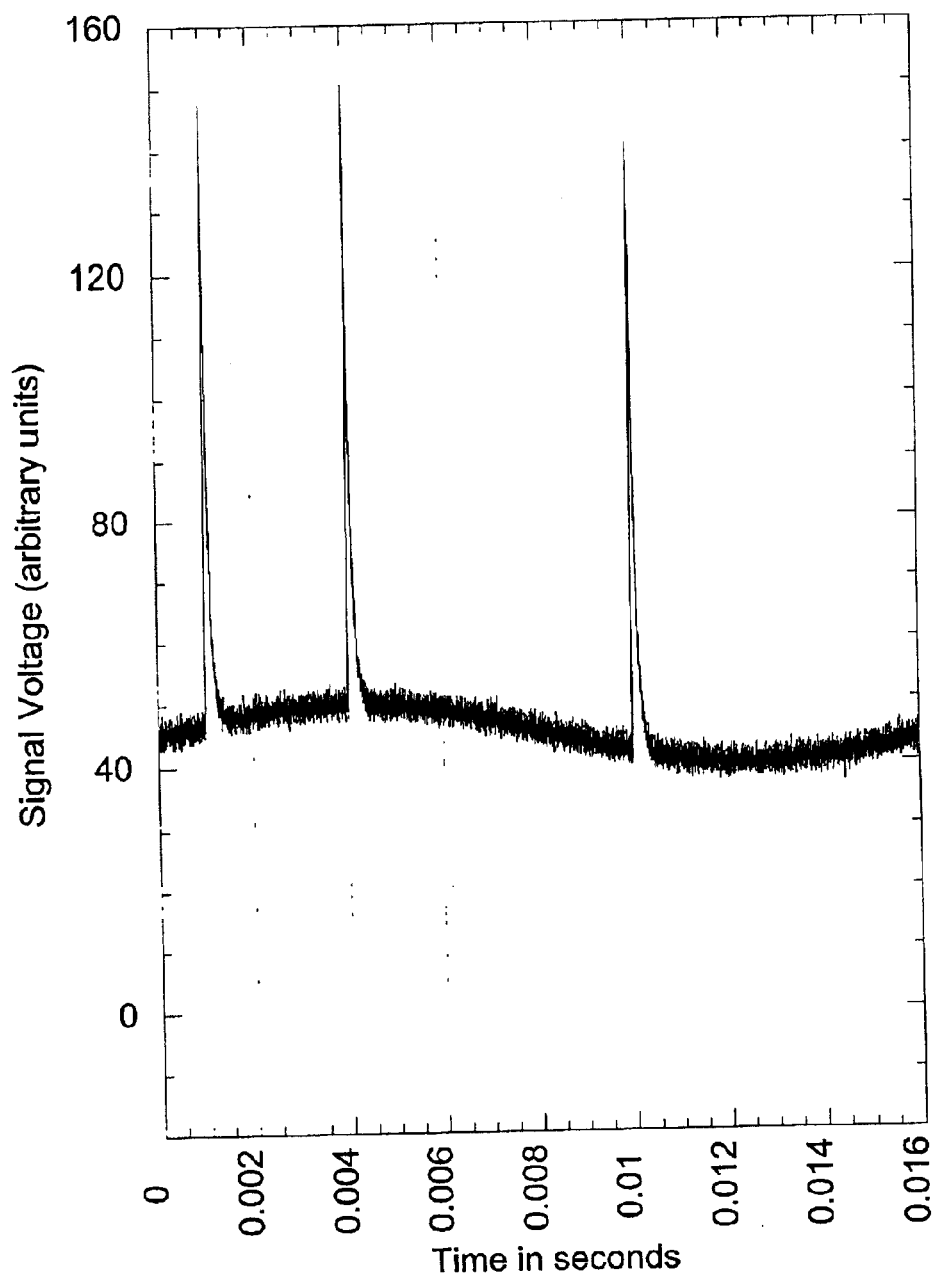
FIG. 3 is a graph depicting a data model of exemplary ring-down signal sequence and noise.

FIG. 3 depicts a measured ring-down signal for the present data model. The measured signal includes the sum of the ring-down signal sequence, a 60-Hz sinusoidal noise signal and broadband random noise signal. Here, it can be seen that the total time for the sum of the ring-down signal sequences is about 0.016 sec, which corresponds to the full period of the sinusoidal noise signal, while each individual ring-down sequence period is substantially shorter. Each of the component parts is depicted separately in FIG. 4, while the sum of each individual ring-down sequence is depicted in FIGS. 5–7.

Figure 4:
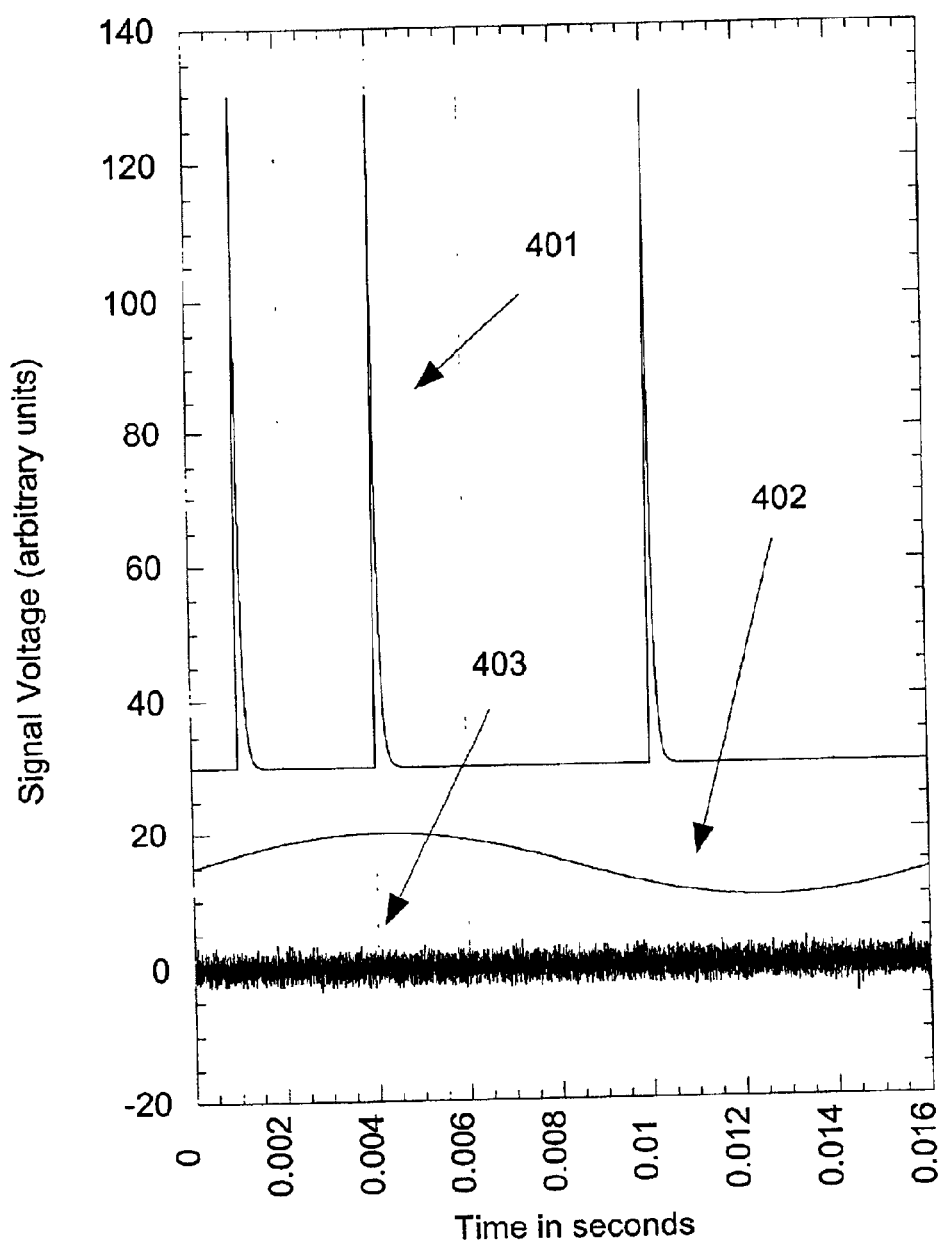
FIG. 4 is a graph depicting a data model of exemplary ring-down signal sequence and noise in component parts.

Turning now to FIG. 4 there is shown an exemplary data model in its component parts including a ring-down signal sequence 401 contaminated with both 60 Hz noise 402 and broadband random noise 403. As measured in arbitrary units, ring-down signal sequence 401 has an amplitude of approximately 100 units with a decay time of 80 microseconds and a 30 unit DC offset. The 60 Hz noise signal has an amplitude of 5 units and a DC offset of 15 units. The broadband random noise signal has a unit standard deviation of 1. As can be seen in the example depicted in FIG. 4, the period of the 60 Hz noise is substantially longer than that of the decay time of a ring-down signal.

Figure 5:
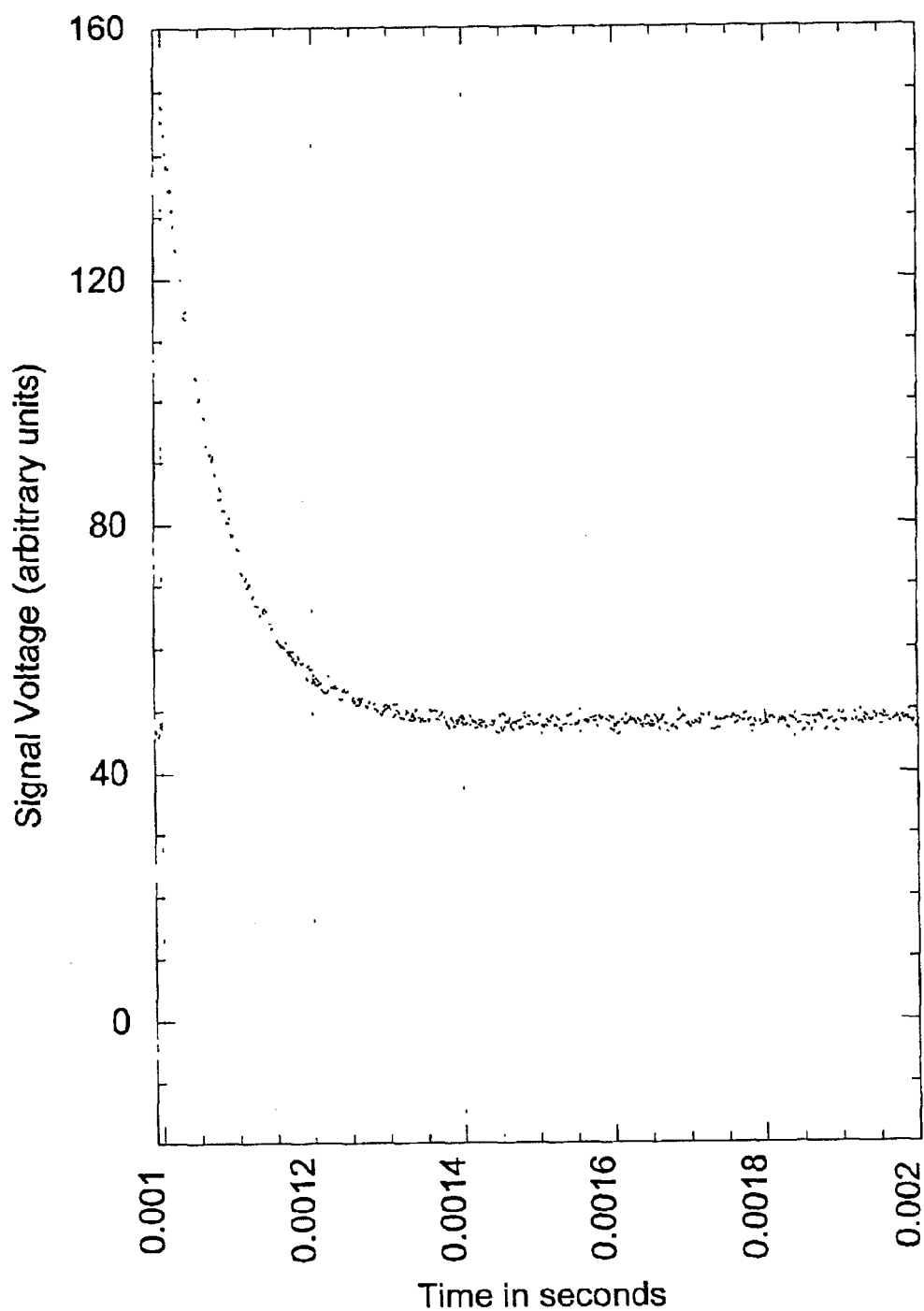
FIG. 5 is an expanded view of the first ring-down signal in FIG. 3.
Figure 6:
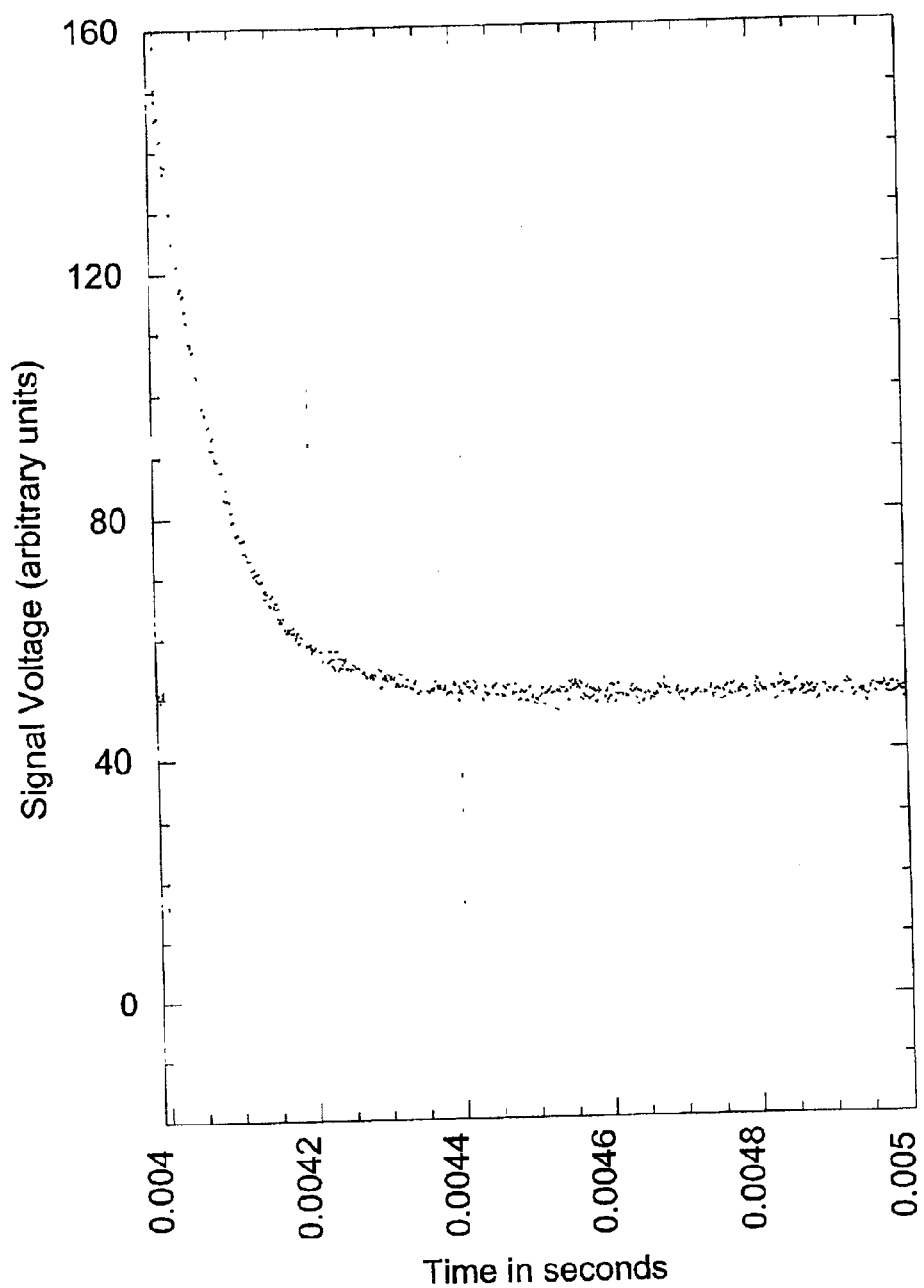
FIG. 6 is an expanded view of the second ring-down signal in FIG. 3.
Figure 7:
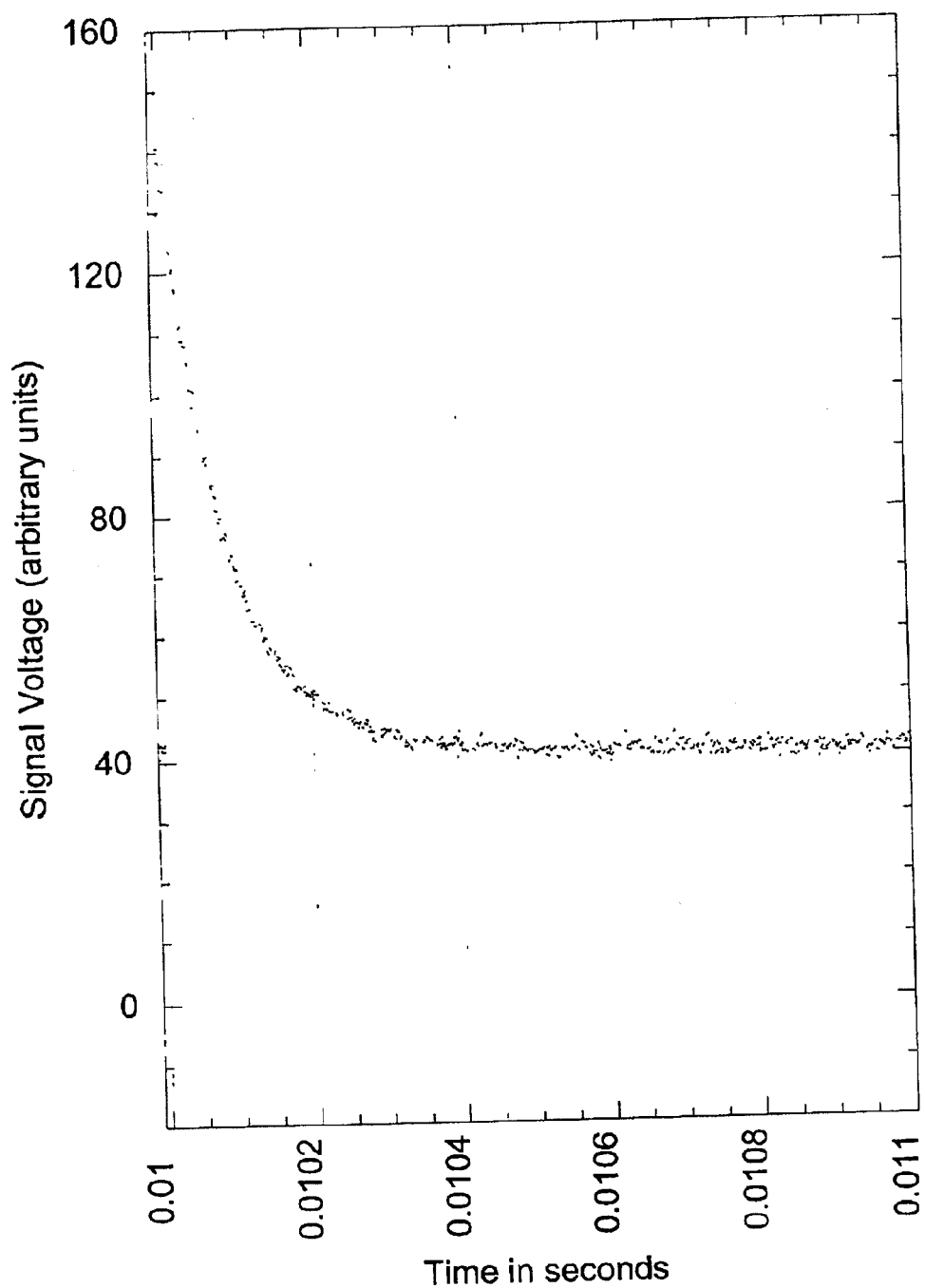
FIG. 7 is an expanded view of the third ring-down signal in FIG. 3.

Each of the separate ring-down sequence signals depicted in FIG. 3 is shown in expanded view in FIGS. 5, 6 and 7. FIG. 5 depicts a typical record for 1 ms on the ascending slope of the sinusoidal noise signal of the first ring-down sequence signal for the time interval of about 0.001 s to 0.002 s. FIG. 6 depicts a typical record for 1 ms near the peak of the sinusoidal noise signal of the second ring-down sequence signal for the time interval of about 0.004 s to 0.005 s. FIG. 7 depicts a typical record for 1 ms on the descending slope of the sinusoidal noise signal of the third ring-down sequence signal for the time interval of about 0.01 s to 0.011 s.

It is shown in FIGS. 5–7, that the algorithm of the present invention can correct for low frequency noise regardless of the exact frequency of that noise or even if it is made up of several frequency components. That is to say that FIGS. 5–7 show that once the ring-down signal has reached a level where the signal to noise ratio approaches values less than 1:1, meaning that only the noise remains, the data points can be measured at any point along the sinusoidal noise signal whether it be ascending, descending or at its peak value. This can be done because the overall slope of the record at any point along the sinusoid approximates a straight line for the short time frame in relation to the entire time for a full period. Accordingly, whether data is extracted on the ascending, descending, or peak of the sinusoidal noise signal the ability to obtain more precise time decay results is not affected. Because the time segment of the record is so small the addition of the sine signal section closely approximates a straight line. Therefore, one can use a straight line approximation beginning from the point of $i_0$ to the end of the record to subtract out the low frequency noise.

Turning now to FIG. 8, there is again shown the first ring-down signal in expanded view. In this figure, the last one hundred points of the record are used to find the average DC offset to subtract from the ring-down data. To find the average DC offset, the average value of the final 100 data points of the measured signal is calculated. The final 100 data points are used, because the ring-down signal will have reached a minimum value at this point. Once the average DC offset is calculated that value is subtracted from the measured signal data points, thereby shifting the measured signal along the y-axis.

Figure 8:
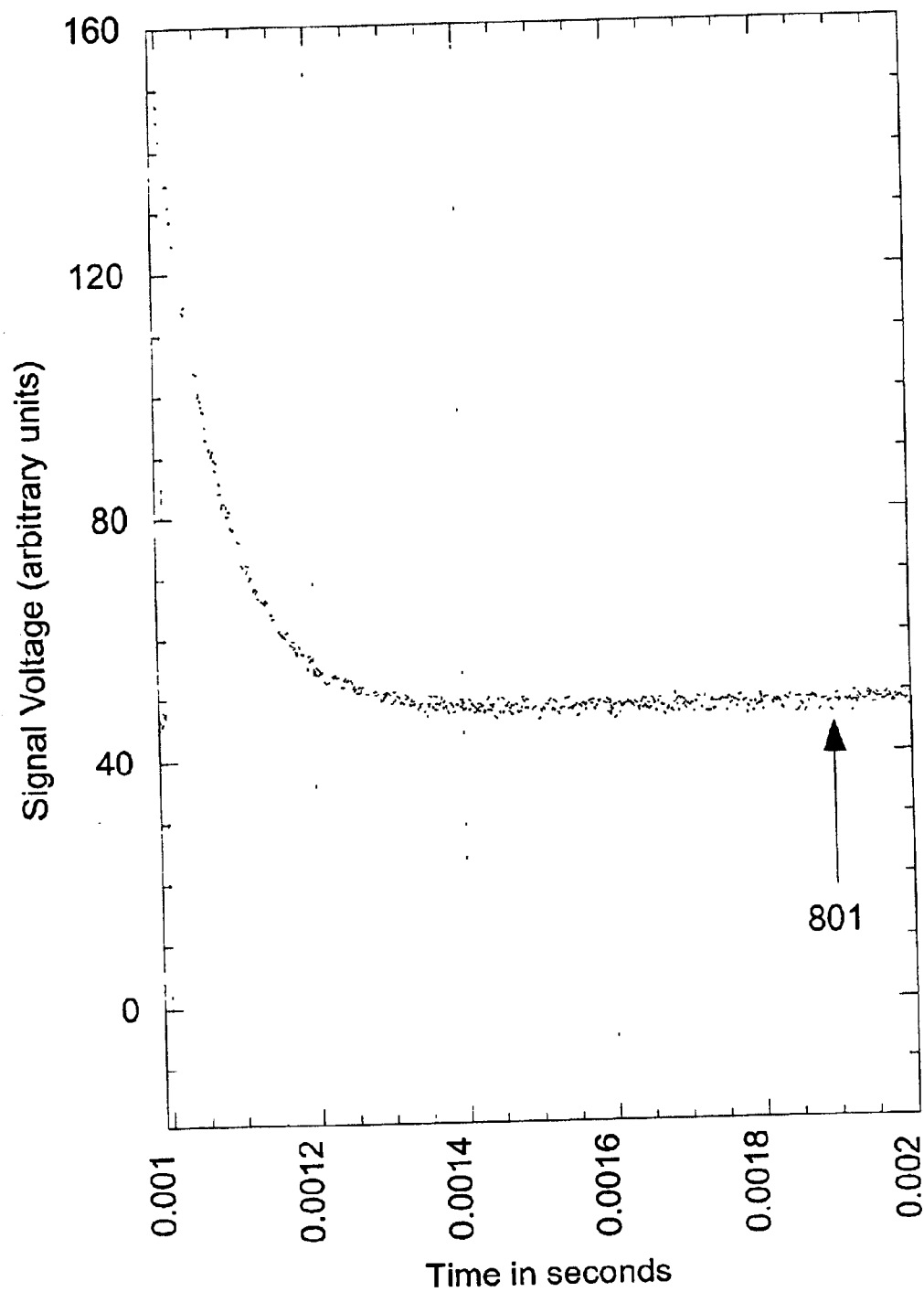
FIG. 8 is an expanded view of the first ring-down signal in FIG. 3.
Figure 9:
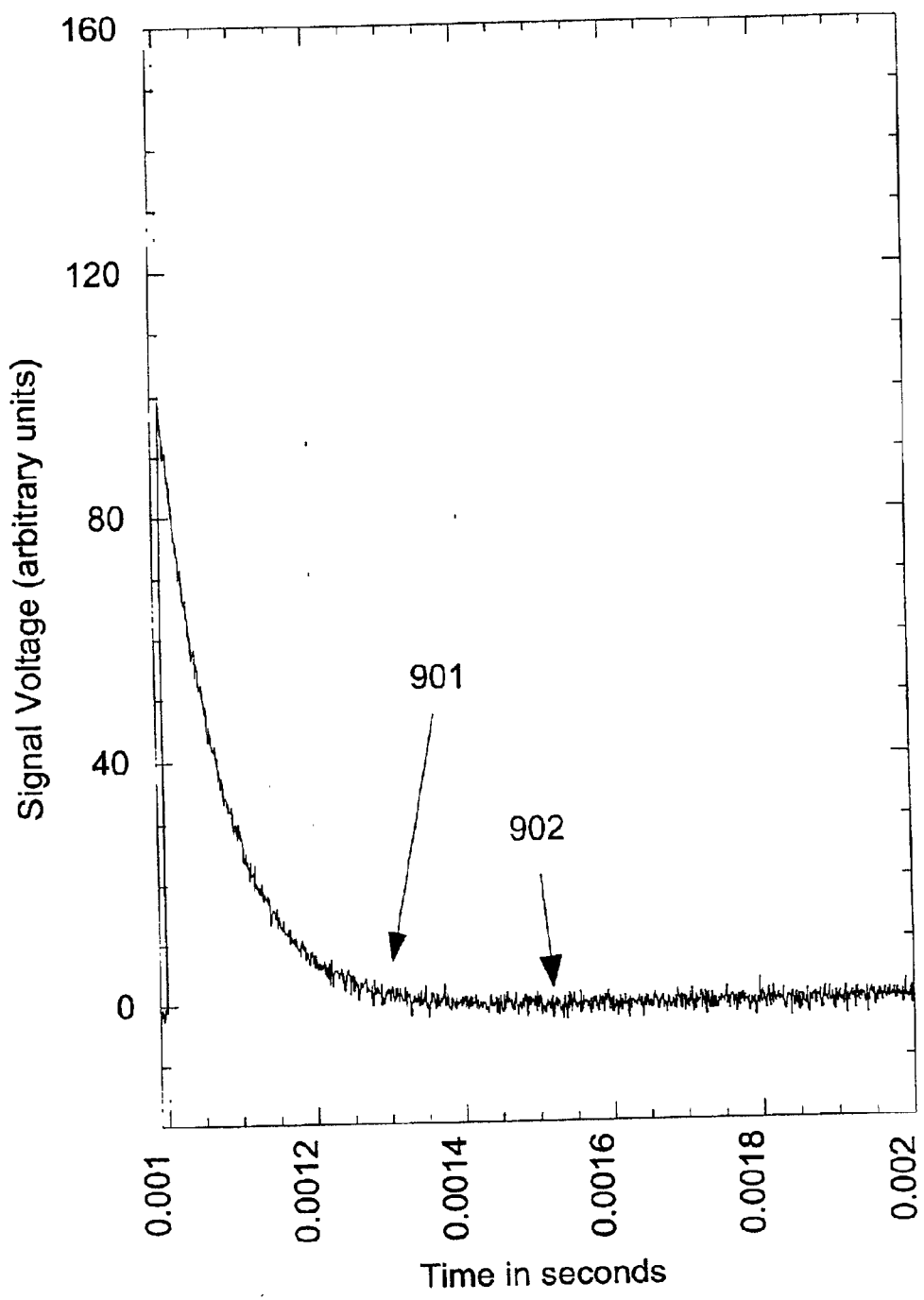
FIG. 9 is an expanded view of the first ring-down signal in FIG. 5 after the DC baseline has been subtracted.

Turning now to FIG. 9, there is shown the ring-down signal of FIG. 8 after the DC offset has been subtracted. The points from the beginning of the shifted record to the point 901 before the first zero or negative value is used in the known algorithm to determine the exponential decay rate or time. According to that method, in this example the last data point that can be used in the logarithmic transformation 901, which corresponds to the point before the first zero or negative point is the $276^{th}$ point of the record. Here, the last hundred points of the record has an average value of 48.491, which is the DC offset to subtract from the data.

Figure 10:
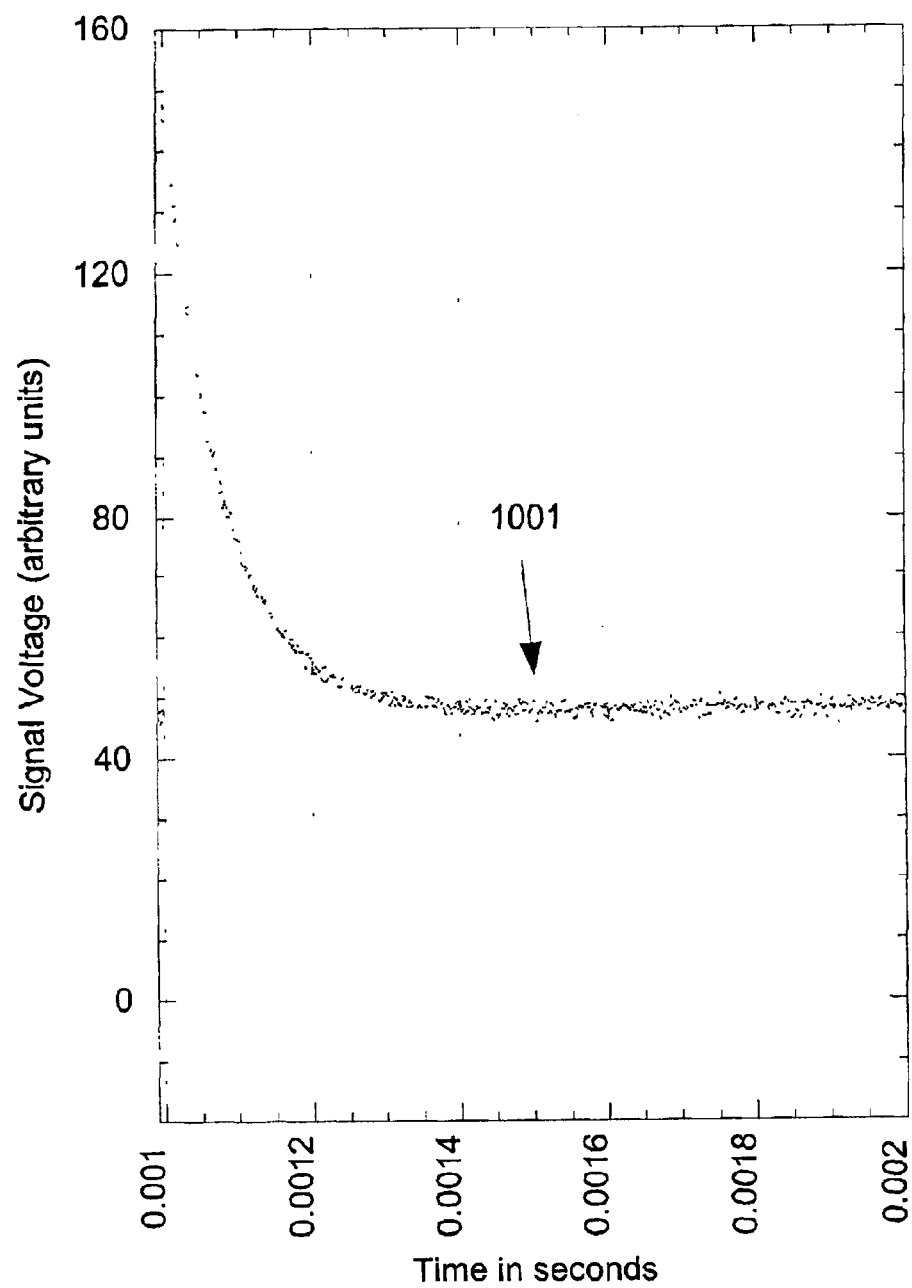
FIG. 10 is an expanded view of the first ring-down signal in FIG. 5.
Figure 11:
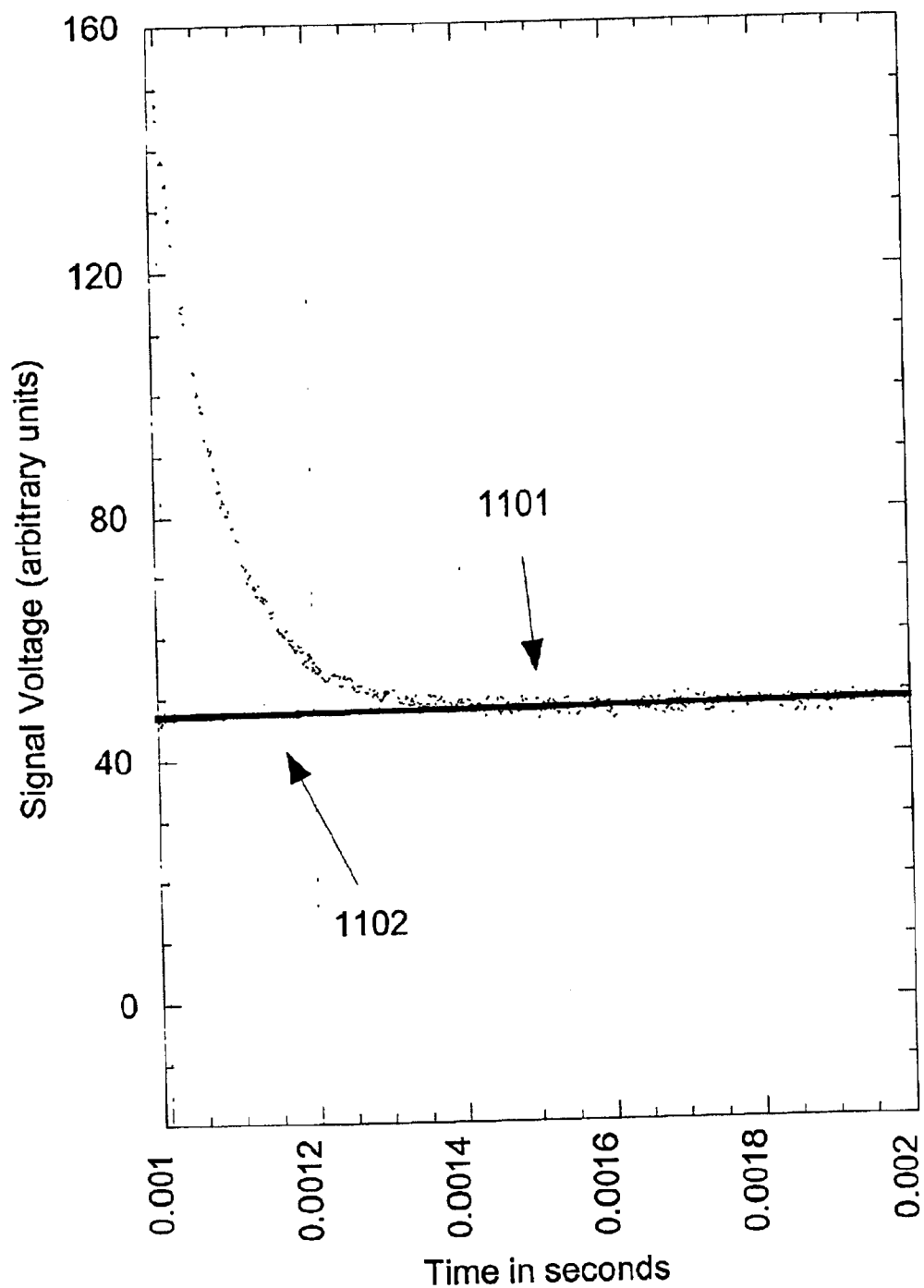
FIG. 11 is an expanded view of the first ring-down signal in FIG. 5 showing a fit line that will be subtracted from the original data.
Figure 12:
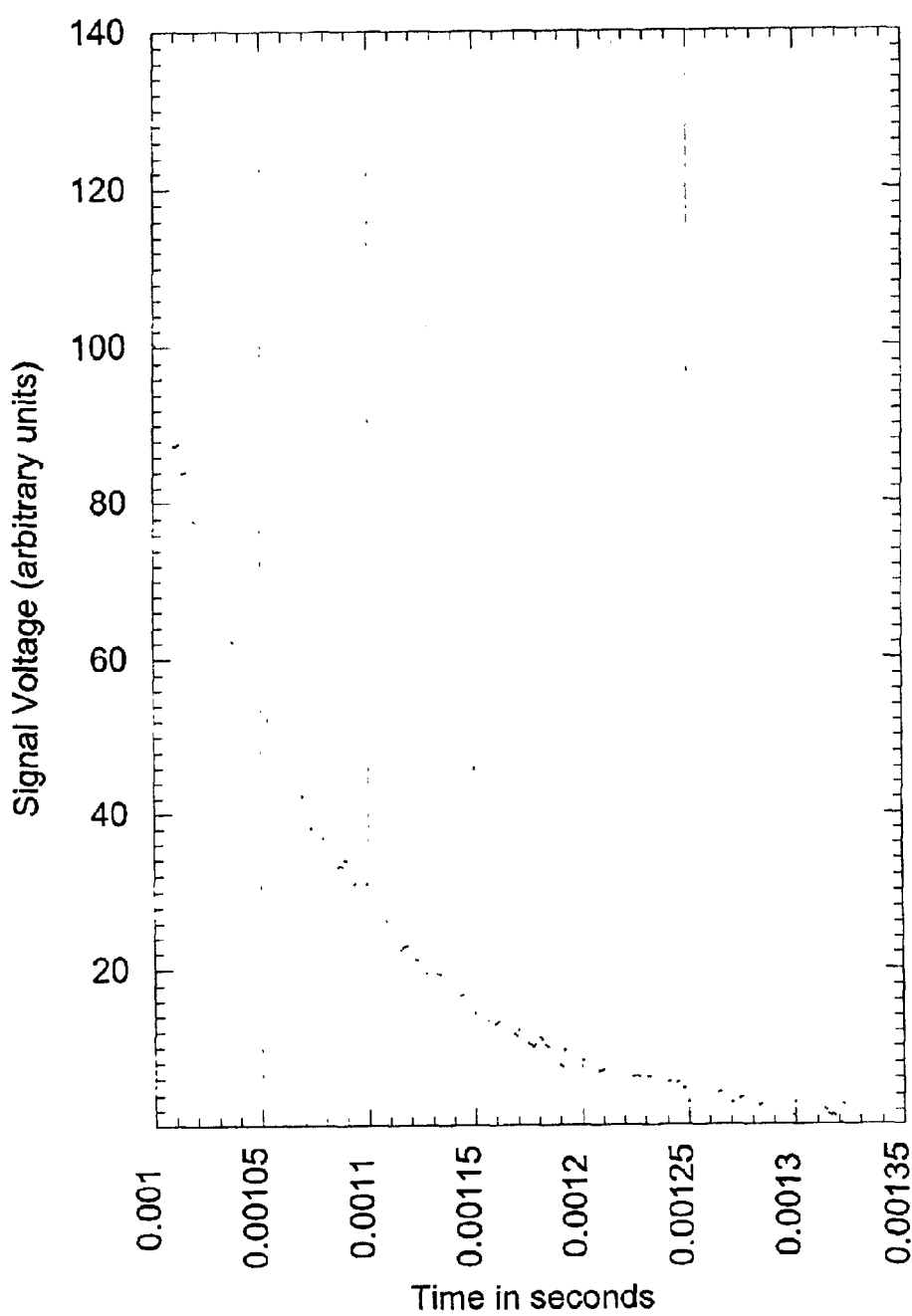
FIG. 12 is a graph of a ring-down signal of FIG. 11 in an expanded view.

FIG. 9 provides an expanded view of FIG. 5, after the DC baseline has been subtracted. The points from the beginning of the record to the point before the first zero or negative value, are used in the standard algorithm to determine the exponential decay rate or time. Here, the first negative value is recorded at 0.001277 seconds, or at the $277^{th}$ point of the record. The time value for the positive point of the record establishing the point before the first zero or negative value is doubled 902. In this example, that time value, 0.001276 sec. is doubled to 0.001552 point of the record, which corresponds to the $552^{nd}$ point, 1001, as shown in FIG. 10. Once that point is determined a straight line is fit to the end of the record for that value 1001. In FIG. 11, that value, 1001 which corresponds to 1101, is then used to find a line 1102 that will be subtracted at each point from the original data as shown in FIG. 11. In FIG. 12, the ringdown signal of FIG. 11 is shown in an expanded view after the fitted line has been subtracted from it. The last positive value is again determined, this time for use in a logarithmic transformation. In this example, the last positive point is at 326. FIG. 13 provides a data model of FIG. 12 for the first 326 points, up to the last positive value, plotted on a logarithmic scale. FIG. 13 also shows how a straight line fit would determine the exponential decay rate of the ringdown signal. The points are to be weighted in proportion to their amplitude in the fitting process, accentuating the higher valued points. The techniques of the present invention described herein may be implemented in hardware or software, or a combination of the two, but are not limited to any particular hardware or software configuration. The foregoing descriptions of the specific embodiments of the present invention have been presented for purposes of illustration and description only. They are not intended to be exhaustive or to limit the invention to the precise forms disclosed, and obviously many modifications and variations are possible in light of the above teaching. The embodiments were chosen and described to best explain the principles of the invention and its practical application, to thereby enable one of ordinary skill in the art to best utilize various embodiments with various modifications as are suited to the particular use contemplated. It is intended that the scope of the invention be defined by the claims appended hereto and their equivalents.

What is claimed is:

1. A method for determining an exponential decay rate of a signal in the presence of noise, said method comprising:

receiving an exponentially decaying signal from a detector;

digitizing said signal to form a first array of data points;

estimating a baseline value of said signal by averaging a final fraction of said data points;

subtracting said baseline value from said first array to generate a second array;

identifying a last data point on said second array occurring before a negative or nil valued data point on said second array;

scaling an ordinate value of said last data point by a factor greater than unity to determine a new first data point for a baseline fit on said first array;

fitting remaining data on said first array to a straight line to determine an estimate for a sloping baseline and said noise;

subtracting said straight line from said data points to establish a resulting array;

identifying a last data point on said resulting array occurring before a negative or nil valued data point on said resulting array;

performing a logarithmic transformation of said resulting array up to said last data point on said resulting array; and determining said decay rate of said signal;

wherein said noise includes broadband noise and excess low frequency noise and wherein said low frequency noise has spectral components having a period greater than four times a record length.

2. The method of claim 1 wherein said determining step includes determining said decay rate of said signal by a weighted least squares fit to said transformed data.

3. The method of claim 2 wherein said weighted least squares fit includes weighting each transformed data point inversely proportional to a square of said value of said digitized signal minus said estimated baseline value.

4. The method of claim 1 wherein said signal is generated in a ring-down cell.

5. The method of claim 4 wherein said ring-down cell includes two or more mirrors in any geometry that produces a stable optical cavity.

6. The method of claim 4 further comprising energizing said ring-down cell.

7. The method of claim 6 wherein said energizing step includes utilizing a laser.

8. The method of claim 6 wherein said laser is a continuous wave laser.

9. The method of claim 6 wherein said laser is a pulsed laser.

10. The method of claim 1 wherein said detector includes a photodector.

11. The method of claim 1 further comprising removing transient points from said first array.

12. The method of claim 11 wherein said subtracting a baseline value includes subtracting a DC level.

13. The method of claim 1 wherein said subtracting a baseline value includes subtracting a DC level.

* * * * *